United States Patent [19]

Burgeson et al.

[11] Patent Number: 5,580,960
[45] Date of Patent: Dec. 3, 1996

[54] KS-LAMININ AND METHODS OF USE

[75] Inventors: Robert E. Burgeson, Charlestown; Marie-France Champliaud, Boston, both of Mass.

[73] Assignee: The General Hospital Corporation, Boston, Mass.

[21] Appl. No.: 141,233

[22] Filed: Oct. 22, 1993

[51] Int. Cl.$^6$ .......................... C07K 14/78; C07K 14/47; A61K 38/39; A61K 38/17
[52] U.S. Cl. .......................... 530/395; 530/350; 530/842; 530/851; 530/353
[58] Field of Search .............................. 530/388.2, 388.9, 530/389.8, 389.1, 350, 395, 352, 842, 851, 353; 435/70.21, 172.2, 240.27; 514/8, 21

[56] References Cited

U.S. PATENT DOCUMENTS 5,003,044   3/1991   Hunter et al. ........................... 530/326

FOREIGN PATENT DOCUMENTS

WO92/17498   10/1992   WIPO .

OTHER PUBLICATIONS

Marinkovich et al., "The Anchoring Filament Protein Kalinin Is Synthesized and Secreted as a High Molecular Weight Precursor" *Journal of Biological Chemistry*, vol. 267, No. 25, pp. 17900–17906, 1992.
Hunter et al., "Laminin Chain Assembly by Triple and Double Stranded Coiled–Coil Structures" *The Journal of Biological Chemistry*, vol. 267, No. 9, pp. 6006–6011, 1992.
Hunter et al., "Expression of S–Laminin and Laminin in the Developing Rat Central Nervous System" *The Journal of Comparative Neurology*, vol. 323, pp. 238–251, 1992.
Marinkovich et al., "The Dermal–Epidermal Junction of Human Skin Contains a Novel Laminin Variant" *The Journal of Cell Biology*, vol. 119, No. 3, pp. 695–703, 1992.
Hunter et al., "An LRE (Leucine–Arginine–Glutamate)–dependent Mechanism for Adhesion of Neurons to S–laminin" *The Journal of Neuroscience*, vol. 11, No. 12, pp. 3960–3671, 1991.
Rouselle et al., "Kalinin: An Epithelium–Specific Basement Membrane Adhesion Molecule That Is a Component of Anchoring Filaments" *Journal Cell Biology*, vol. 114, pp. 567–576, 1991.
Engvall et al., "Distribution and Isolation of Four Laminin Variants; Tissue Restricted Distribution of Heterotrimers Assembled From Five Different Subunits" *Cell Regulation*, vol. 1, pp. 731–740, 1990.
Ehrig et al., "Merosin, A Tissue–Specific Basement Membrane Protein, is a Laminin–Like Protein" *Proceedings of the National Academy of Sciences*, vol. 87, pp. 3264–3268, 1990.
Beck et al., "Structure and Function of Laminin: Anatomy of a Multidomain Glycoprotein" *The FASEB Journal*, vol. 4, pp. 148–160, 1990.
Sanes et al., "S–Laminin" *Cold Spring Harbor Symposia on Quantitative Biology*, vol. 55, pp. 419–430, 1990.

Liesi et al., "Glial Cells of Mammalian Brain Produce a Variant Form of Laminin" *Experimental Neurology*, vol. 105, pp. 86–92, 1989.
Paulsson et al., "Mouse Heart Laminin" *The Journal of Biological Chemistry*, vol. 264, No. 31, pp. 18726–18732, 1989.
Hunter et al., "Primary Sequence of a Motor Neuron–Selective Adhesive Site in the Synaptic Basal Protein S–Laminin" *Cell*, vol. 59, pp. 905–913, 1989.
Frenette et al., "Biosynthesis and Secretion of Laminin and Laminin–associated Glycoproteins by Nonmalignant and Malignant Human Keratinocytes: Comparison of Cell Lines from Primary and Secondary Tumors in the Same Patient" *Cancer Research*, vol. 48, pp. 5193–5202, 1988.
Woodley et al., "Laminin Inhibits Human Keratinocyte Migration" *Journal of Cellular Physiology*, vol. 136, pp. 140–146, 1988.
Aratani et al., "Enhanced Synthesis and Secretion of Type IV Collagen and Entactin during Adipose Conversion of 3T3–L1 Cells and Production of Unorthodox Laminin Complex" *The Journal of Biological Chemistry*, vol. 263, No. 31, pp. 16163–16169, 1988.
Edgar et al., "Structural Requirements for the Stimulation of Neurite Outgrowth by Two Variants of Laminin and Their Inhibition by Antibodies" *The Journal of Cell Biology*, vol. 106, pp. 1299–1306, 1988.
Engvall et al., "Mapping of Domains in Human Laminin Using Monoclonal Anitibodies: Localization of the Neurite–promoting Site" *The Journal of Cell Biology*, vol. 103, No. 6, pp. 2457–2465, 1986.
Davis et al., "Isolation and Characterization of Rat Schwannoma Neurite–promoting Factor: Evidence that the Factor Contains Laminin" *The Journal of Neuroscience*, vol. 5, No. 10, pp. 2662–2671, 1985.
Peters et al., "The Biosynthesis, Processing, and Secretion of Laminin by Human Choriocarcinoma Cells" *The Journal of Biological Chemistry*, vol. 260, No. 27, pp. 14732–14742, 1985.
Morita et al., "Post–translational Assembly and Glycosylation of Laminin Subunits in Parietal Endoderm–like F9 Cells" *Biochemistry Journal*, vol. 229, pp. 259–264, 1985.
Wewer et al., "Human Laminin Isolated in a Nearly Intact, Biologically Active Form from Placenta by Limited Proteolysis" *The Journal of Biological Chemistry*, vol. 258, No. 20, pp. 12654–12660, 1983.
Cooper et al., "Studies on the Biosynthesis of Laminin by Murine Parietal Endoderm Cells" *European Journal of Biochemistry*, vol. 119, pp. 189–197, 1981.
Kleinman et al., Arch. Biochem. and Biophys., vol. 272: 39–45, 1989.
Burgeson et al., Matrix Biology, 14: 209–211, 1994.
Timpl et al., Matrix Biology, 14: 275–281, 1994.
Marinkovich et al., J. Inv. Derm., 96: 551, 1991.

*Primary Examiner*—Ronald B. Schwadron
*Attorney, Agent, or Firm*—Louis Myers

[57] ABSTRACT

KS-laminin and a KS-laminin-kalinin adduct are disclosed. The molecules of the invention are useful for promoting the adhesion of keratinocytes to a substrate.

1 Claim, No Drawings

KS-LAMININ AND METHODS OF USE

This invention was made with government support. The U.S. government may have certain rights in this invention.

BACKGROUND OF THE INVENTION

The present invention relates to adhesion proteins and to methods of using them to promote the adhesion of keratinocytes to a substrate, e.g., to human dermis. In particular, KS-laminin, a new variant of laminin is disclosed.

Laminins are multimeric proteins involved in the adhesion between the human dermis and epidermis. Laminins generally includes three sub-units, a B1 chain, a B2 chain, an A chain. There are two known variants of B1 chain, the prototypic B1 exemplified by the B1e chain present in Englebreth-Holm-Swarm tumor laminin, (EHS-laminin) (Cooper et al., *Eur. J. Bio. Chem.* 119:189 (1981)); and B1s, exemplified by the B1 chain of S-laminin, a variant with 80% homology to EHS B1. The prototype B2 chain is the B2e chain of EHS-laminin. Laminin A chains includes the prototypic laminin A, referred to as Ae, found in EHS-laminin and, a laminin A variant called Merosin A, which is about 40% homologous with the Ae chain.

Variants laminins include Merosin laminin, mouse heart laminin, and S-laminin. Merosin contains a B1e chain, a B2e chain, and a third chain, called Merosin A. This chain is distinct from the EHS-laminin A chain, and shares only about 30% homology by sequence analysis. (Ehrig et al., *Proc. Natl. Acad. Sci.* 87:3264–3268 (1990)). Mouse heart laminin is a laminin with a substituted A chain. (Saladin et al., *J. Biol. Chem.* 264:18726–18732 (1989)). S-laminin contains the EHS-laminin B2e and Ae chains, and a variant B1 chain, B1s, which shows some sequence homology to the EHS-B1e chain (Hunter et al., *Nature* 338:222–234). Recently, another variant of laminin comprising a complex of the S-laminin B1s chain, the EHS B2e chain, and the merosin A chain was also isolated from certain tissues, including the myotendonous junction (Engvall et al., *Cell Regulation.* 1:731–740 (1990)). Three other variants, rat RN22 laminin (Davis et al., *J. Neuroscience* 5:2662 (1985); Edgar et al., *J. Cell Biol.* 106:1299 (1988)), 3T3 adipocyte laminin (Aratani et al, *J. Biol. Chem.* 263:16163 (1988)), and rat astrocyte laminin (Liesi et al., *Exp. Neurol.* 105:86–92 (1989)), have also been reported.

SUMMARY OF THE INVENTION

In general, the invention features a purified KS-laminin which includes: a B1 chain which reacts with an antibody to the B1s chain of S-laminin (the anti-B1s antibody preferably does not react with other B1 chains, e.g., B1e); a B2 chain which reacts with an antibody to the B2e chain of EHS-laminin (the anti-B2e antibody preferably does not react with other B2 chains); and an A chain which reacts with an antibody to a Kalinin A chain (the anti-kalinin A antibody preferably does not react with laminin A chains, e.g., Ae or Merosin A).

In preferred embodiments: the anti-B1s antibody is a monoclonal antibody e.g., maB C4 or a monoclonal antibody with substantially the same ability to distinguish B1s from B1e; the anti-B2e antibody is a polyclonal anti-laminin antibody or an anti-B2e antibody, e.g., a monoclonal anti-B2e antibody, and the anti-A chain antibody is a monoclonal antibody, e.g., BM165 or a monoclonal antibody with substantially the same ability to distinguish kalinin A from laminin A.

In preferred embodiments: the B1, B2 and A chains are present in a ratio of about 1 B1 to 1 B to 1 A; the B1, B2 and A chains, when reduced under conditions that break disulfide linkages, produce chains B1s, B2e and A with electrophoretic band B1s at 190 kDa, band B2e at 220 kDa and band A at 165 kDa; the purified KS-laminin has a Y-shaped rotary shadow image with a long arm and first and second short arms; the KS-laminin naturally occurs in human amnion; the invention further includes a kalinin molecule covalently associated with the KS-laminin; the KS-laminin is isolated from amnion; the KS-laminin is mammalian, e.g., primate, e.g., human, KS-laminin; the KS-laminin promotes the adhesion of a cell, e.g., a keratinocyte, to a substrate.

In another aspect, the invention features a purified KS-laminin which includes: a B1 chain substantially identical with the B1s chain of S-laminin; a B2 chain substantially identical with the B2 chain of EHS-laminin; and an A chain substantially identical with an A chain of kalinin.

In preferred embodiments: the B1, B2 and A chains are present in a ratio of about 1 B1 to 1 B2 to 1 A; the B1, B2 and A chains, when reduced under conditions that break disulfide linkages, produce chains B1s, B2e and A with electrophoretic band B1s at 190 kDa, band B2e at 220 kDa and band A at 165 kDa; the purified KS-laminin has a Y-shaped rotary shadow image with a long arm and first and second short arms; the KS-laminin is immunoreactive with an antibody to kalinin A, e.g., monoclonal antibody BM165 or a similar antibody, but not to an antibody to kalinin B1, e.g., monoclonal antibody K140 or a similar antibody; the KS-laminin is immunoreactive with an anti-B1s antibody, e.g., mAb C4 or a similar antibody but not with an antibody to other B1 chains, e.g., to B1e; the KS-laminin is immunoreactive with an anti-laminin antibody which identifies the B2e chain; the KS-laminin naturally occurs in human amnion; the invention further includes a kalinin molecule covalently associated with the KS-laminin; the KS-laminin is isolated from amnion; the KS-laminin is mammalian, e.g., primate, e.g., human, KS-laminin; the KS-laminin promotes the adhesion of a cell, e.g., a keratinocyte, to a substrate.

In another aspect the invention features a purified KS-laminin which includes: a B1 chain substantially electrophoretically identical with the B1s chain of S-laminin; a B2 chain substantially electrophoretically identical with the B2e chain of EHS-laminin; and an A chain substantially electrophoretically identical with an A chain of kalinin.

In preferred embodiments: the B1, B2 and A chains are present in a ratio of about 1 B1 to 1 B2 to 1 A; the B1, B2 and A chains, when reduced under conditions that break disulfide linkages, produce chains B1s, B2e and A with electrophoretic band B1s at 190 kDa, band B2e at 220 kDa and band A at 165 kDa; the purified KS-laminin has a Y-shaped rotary shadow image with a long arm and first and second short arms; the KS-laminin is immunoreactive with an antibody to kalinin A e.g., monoclonal antibody BM165 or a similar antibody, but not to an antibody to laminin A, e.g., monoclonal antibody K140 or a similar antibody; the KS-laminin is immunoreactive with an anti-B1s antibody, e.g., mAb C4 or a similar antibody but not with an antibody to other B1 chains, e.g., to B1e; the KS-laminin is immunoreactive with an anti-laminin antibody which identifies the B2e chain; the KS-laminin naturally occurs in human amnion; the invention further includes a kalinin molecule covalently associated with the KS-laminin; the KS-laminin is isolated from amnion; the KS-laminin is mammalian, e.g., primate, e.g., human, KS-laminin; the KS-laminin promotes the adhesion of a cell, e.g., a keratinocyte, to a substrate.

In another aspect the invention features a purified KS-laminin which features: a B1 chain having an amino acid sequence substantially identical with all or part of the amino acid sequence of the B1s chain of S-laminin; a B2 chain having an amino acid sequence substantially identical with all or part of the B2 chain of EHS-laminin; and an A chain having an amino acid sequence substantially identical with all or part of an A chain of kalinin.

In preferred embodiments: the B1, B2 and A chains are present in a ratio of about 1 B1 to 1 B2 to 1 A; the B1, B2 and A chains, when reduced under conditions that break disulfide linkages, produce chains B1s, B2e and A with electrophoretic band B1s at 190 kDa, band B2e at 220 kDa and band A at 165 kDa; the purified KS-laminin has a Y-shaped rotary shadow image with a long arm and first and second short arms; the KS-laminin is immunoreactive with an antibody to kalinin A, e.g., monoclonal antibody BM165 or a similar antibody, but not to an antibody to kalinin B1, e.g., monoclonal antibody K140 or a similar antibody; the KS-laminin is immunoreactive with an anti-B1s antibody, e.g., mAb C4 or a similar antibody but not with an antibody to other B1 chains, e.g., to B1e; the KS-laminin is immunoreactive with an anti-laminin antibody which identifies the B2e chain; the KS-laminin naturally occurs in human amnion; the invention further includes a kalinin molecule covalently associated with the KS-laminin; the KS-laminin is isolated from amnion; the KS-laminin is mammalian, e.g., primate, e.g., human, KS-laminin; the KS-laminin promotes the adhesion of a cell, e.g., a keratinocyte, to a substrate.

In another aspect, the invention features a purified KS-laminin which is derived from amnion, having a molecular weight of about 600 kDa, and which consists of a first chain substantially electrophoretically identical to a B1s, 190 kDa chain of S-laminin, a second 220 kDa chain of laminin B2e, and a third chain of 145 kDa which is not immunoreactive with antibodies to laminin A, e.g., mAbs 1F5, 11D5, and 4C7, but which is reactive with antibodies to kalinin A e.g., monoclonal antibody BM 165, the B1, B2, the chains being present in a ratio of about 1 chain of B1 to 1 chain of B2 to 1 third chain, and having a rotary shadow image having one long arm and two short arms.

In another aspect, the invention features, a covalent, disulfide bonded covalent adduct of kalinin and KS-laminin.

In preferred embodiments: the adduct includes a first electrophoretic chain substantially electrophoretically identical to a B1s chain of S-laminin, and a second electrophoretic chain substantially electrophoretically identical to a B2e chain of laminin, and a third chain of 165 kDa that is not immunoreactive with antibodies against laminin A, e.g., monoclonal antibodies 1F5, 11D5 and 4C7, but is immunoreactive with a monoclonal antibody to kalinin A, e.g., BM 165; and a kalinin molecule covalently attached to the laminin variant by a disulfide bond, wherein the kalinin molecule isolated from the laminin variant has a molecular weight of about 410–460 kDa, and separates on western blots into fragments of 165 kDa, 145 kDa, 140 kDa and 105 kDa under reducing conditions; the adduct naturally occurs in human amnion; the adduct is isolated from amnion; the adduct is a mammalian, e.g., primate, e.g., human, KS-laminin-kalinin adduct; the adduct promotes the adhesion of a cell, e.g., a keratinocyte, to a substrate.

In another aspect, the invention features a method of improving or promoting the adhesion of cells, e.g., transplanted cells, e.g., transplanted skin cells, e.g., keratinocytes, to a substrate, e.g., an underlying substrate. The method includes the step of contacting the cells or the substrate with an effective amount of KS-laminin or KS-laminin-kalinin adduct.

In preferred embodiments: the amount of KS-laminin administered results in an increase in the amount of KS-laminin in or on the cells; the cells are in vitro; the method further includes providing purified KS laminin or a purified covalent adduct of KS-laminin and kalinin; the substrate is an inanimate object, e.g., the surface of a container; the substrate is human tissue, e.g., dermis or subcutaneous tissue; the substrate is the surface of a burn wound; the method further includes the step of providing KS-laminin or a KS-laminin-kalinin adduct in a pharmaceutically acceptable carrier in a concentration of at least 1–10 µg/ml, e.g., at a concentration of KS-laminin is at least 40 µg/ml; the adduct of KS-laminin and kalinin is provided in a pharmaceutically acceptable carrier in an amount of at least 40 µg/ml; the method further includes administering a second adhesion molecule, e.g., is K-laminin.

In another aspect, the invention features a method of purifying KS-laminin or the adduct of KS-laminin and kalinin including: applying a fraction tissue, e.g., of amnion, e.g., a soluble fraction of amnion, to an ion exchange column, e.g., a MONO-Q HPLC ion exchange column. The invention also features KS-laminin and an adduct of KS-laminin and kalinin purified by the method.

In another aspect, the invention features a method of purifying KS-laminin or the adduct of KS-laminin and kalinin comprising a step of applying a fraction, preferably a soluble fraction, of a tissue, e.g., of amnion, to an immunoaffinity column bearing an anti-B1s antibody and recovering the product by its affinity for the antibody. In preferred embodiments, the anti-B1s antibody is monoclonal antibody, e.g., mAb C4 or a substantially similar antibody; the source of said KS-laminin is amnion; the method further includes contacting the fraction with an anti-kalinin A antibody. The invention also includes KS-laminin and an adduct of KS-laminin and kalinin purified by this method.

As used herein, an antigen is "immunoreactive" with an antibody if it is immunoprecipitated by the antibody, for example, in SDS-PAGE or if it reacts by Western blot if SDS-PAGE resolved proteins.

A "purified" molecule, such as purified K-laminin, is one that is sufficiently purified that it is free of other molecules that it is associated with in vivo. An example of a purified molecule is one that has been subjected to immunoaffinity separation to separate substantially all proteins except for the isolated species. The covalently associated kalinin-KS-laminin is purified when it is substantially free of other proteins that are found in the environment of this complex in vivo.

Electrophoresis bands are "substantially electrophoretically identical" when they produce substantially identical band patterns when exposed to and reacted with substantially identical antibodies, e.g., substantially identical monoclonal antibodies.

Reaction between an antibody and an antigen refers to an antigen-antibody interaction.

An adduct is a covalently bound complex.

The present invention features a new laminin variant, KS-laminin, a KS-laminin-kalinin adduct, and methods of purifying both. These molecules are useful for promoting the adhesion of keratinocytes to a substrate. In particular, these molecules are useful for promoting the successful adhesion of keratinocyte autografts to human dermis. The molecules are also useful for research in cell adhesion.

Other features and advantages of the invention will be apparent from the following description and from the claims.

DETAILED DESCRIPTION OF THE INVENTION

Purification of KS-laminin

The purification of the KS-laminin and KS-laminin-kalinin adducts was carried as follows. Human amnions were frozen in liquid nitrogen, ground in a WARING™ blender and washed in 1M NaCl. The final tissue pellet (200 g, wet weight) was suspended in 1 liter of extraction buffer (50 mM Tris-HCl 50 mM, pH=7.8; $CaCl_2$ 5 mM, 625 mg/l of N-ethylmaleimide, 150 mg/l of phenylmethylsulphonyl fluoride and 4,000 U of bacterial collagenase (CLSPA, Worthington Biochemical)). The suspension was incubated at room temperature with stirring, and after 24 hours, an additional 4,000 units of enzyme was added. The extraction was continued for another 24 hours. Unless otherwise noted, all subsequent steps were performed at 4° C. The soluble fraction was collected following centrifugation (30,000×g, for 60 minutes) and precipitated by 300 g/l of ammonium sulfate. The precipitated proteins were collected following centrifugation (30000×g, for 60 minutes) and redissolved into chromatography buffer (2M urea, 25 mM NaCl, 5 mM EDTA, and 50 mM Tris-HCl, pH=7.8). The extracted proteins were treated with difluorophopsphate (5 mg/l) and then dialyzed against chromatography buffer. Following dialysis, 0.5 volume of buffer equilibrated DEAE-cellulose (DE-52, Whatman) was added and the mixture was shaken overnight. Material not bound to DEAE-cellulose was collected by filtration on a Buchner funnel (Whatman filter 4) and precipitated by addition of 300 g/l of ammonium sulfate. The proteins were collected following centrifugation (30,000×g, for 60 minutes), redissolved in the Concanavalin-A buffer (0.5M NaCl, 5 mM $CaCl_2$, 5 mM $MgCl_2$, and Tris-HCl 50 mM, pH=7.8) and dialyzed against the same buffer overnight. The fraction was applied to a 2.5×5 cm Concanavalin-A SEPHAROSE column (Pharmacia), and unbound material was discarded. The column was first eluted with 10 mM α-D-mannopyrannoside (Sigma), washed, and then eluted with 1M α-D-glucopyrannoside (Sigma). A third wash with 1M α-D-mannopyrannoside (Sigma) contained the proteins of interest. This fraction was concentrated to 10 ml on a AMICON™ concentrator (30 kDa membrane) and applied on a 2.5×100 cm SEPHACRYL™ S-500 column in a 0.5M NaCl, 50 mM Tris-HCl, pH=7.8 buffer. The fractions of interest were pooled, (fractions are chosen by assaying them by SDS-PAGE to determine which contain the protein of interest) dialysed against MONO-Q™ buffer (0.1M NaCl, 25 mM Tris-HCl, pH7.8) and applied to a 1×5 cm MONO-Q™ column (Pharmacia). Elution was realized by a 60 ml gradient (0.1–0.5M NaCl).

Characterization of KS-laminin

Kalinin containing complexes from human amnion were partially fractionated by HPLC MONO-Q™ ion exchange chromatography. (The steps previous to MONO-Q™ allow purification of the two complexes from other proteins solublized from amnion. The ion exchange step allows separation of the two complexes.) The materials eluted as two overlapping peaks, one at about 0.075 and another at about 0.125M NaCl. Electrophoretic gel analysis of alternate fractions across the peaks indicated two dominant patterns. The first peak eluted contained major bands at 220, 190, 165 and 140 kDa, and a minor band at 105kDa. Western blotting of fraction 10 of the first peak with Kalinin polyclonal Ab confirmed the presence of Kalinin in the peak. Blot positive bands were identified in the position of 165, 145/140 and 105kDa, corresponding to the processed forms of kalinin A chain (165/145 kDa), kalinin B1 chain (140 kDa) and the kalinin B2 chain (105 kDa). Also consistent with previous results, the kalinin B2 chain is underrepresented by Coommassie blue staining. The bands at 220 and 190 kDa were not recognized by the anti-kalinin antiserum. The same fraction was immunoblotted with mAb C4 specific for the B1s chain (kindly provided by Dr. Joshua Sanes, Washington University, St. Louis) which identified the 190 kDa band as B1s. The band at 220 kDa was recognized by polyclonal anti-laminin antiserum and is in the position of the B2e chain. Therefore, MONO-Q™ peak 1 contains kalinin and another molecule containing the laminin B1s and B2e chains, but lacking an Ae chain.

The second peak contained major bands at 230, 220, 190, 165, and 145/140 kDa and a minor band at 105kDa. Western blotting confirmed this to be a mixture of kalinin and K-laminin (B1e, B2e, kalinin A chain) as previously described (Marinkovich et al, 1993). The B1s chain was not detected in the peak 2 fractions sufficiently removed from spillover from peak 1.

Antibodies

Antibodies, e.g., monoclonal antibodies, against the subunits of KS-laminin can be prepared by preparing KS-laminin as described herein, separating the chains by SDS-PAGE under reducing conditions, excising the appropriate band form the gel, and using the material in the band to generate antibodies by prior art methods. The band 190 kDa contains B1s and can be used to make anti B1s antibodies, the band at 220 kDa contains B2e and can be used to make B2e antibodies, and the band at 165 kDa contains the A chain and can be used to make antibodies against the A chain.

Similar methods can be used to make kalinin antibodies or antibodies to other laminin subunits.

Kalinin Abs

The mAb BM165 reacts with the 165 kDa A chain of kalinin, as described herein and in Rouselle et al., *J. Cell Biol.* 114:567–576 (1991), which is incorporated by reference. The BM165 mAb, an $IgG_1$ was purified from cell culture supernatants as described elsewhere (Keene et al, *J. Cell Biol.* 113:971–978 (1991)). The BM165 immunogen can be derived from an extract of human amnion, prepared as follows. Collagenase extraction and purification of the NC-1 globular domain of type VII collagen from human amnion has been described previously. Bachinger et al., *J. Biol. Chem.* 265:10095–10101 (1990), which is incorporated herein by reference. During one step of this purification, the extract is incubated with DEAE-cellulose (DE52, Whatman) in a low salt buffer (2M urea, 25 mM NaCl, 5 mM EDTA and 50 mM Tris-HCl, pH 7.8). The unbound fraction was used in the further purification of the NC-1 domain. The DEAE-cellulose was washed with an equal volume of buffer containing 0.2M NaCl and the eluted material was isolated after centrifugation at 17,000×g for 60 minutes. The sample was concentrated 10-fold by ammonium sulfate precipitation (50% saturation) and equilibrated in PBS (phosphate-buffered saline) by dialysis. The resulting complex mixture of proteins served as an immunogen in the preparation of hybridomas against kalinin.

The preparation and specificity of mAb K140, which reacts with the 140 kDa B subunit of kalinin, and rabbit polyclonal antiserum against kalinin, are as described in Marinkovich et al. (1992) *J. Biol. Chem.* 267:17900–17906, and as follows. Immunogen necessary to prepare "K140" mAbs was purified from human amnion. Collagenenase-extracted human amnionic membranes were processed by a procedure adapted from Bachinger et al., *J. Biol. Chem.* 256:100095–10101 (1990). Proteins were precipitated from the initial soluble fraction by the addition of ammonium sulfate to a final concentration of 30% (w/v) and incubated overnight at 4° C. Precipitated materials were recovered following centrifugation (17,000×g, for 60 minutes) and resuspended in chromatography buffer prior to dialysis, which greatly decreased the overall viscosity of the sample, presumably due to the removal of nucleic acids. Remaining insoluble material was removed from the sample by ultracentrifugation (18,000 rpm, for 1 hour) in a Beckman Type 19 rotor. The resulting immunogen was used to inoculate two Balb/C mice. Hybridomas were prepared and screened initially by indirect immunofluorescent microscopy according to Sakai et al., *J. Cell Biol.* 103:1577–1586 (1986). One hybridoma named "K140" produced a mAb that specifically recognized the 140-kDa subunit of Kalinin.

Laminin B1 Abs

MAb 545 specific to the B1e chain of human laminin has been described by Marinkovich et al. (1992) *J. Cell Biol.* 119:695–703. Antigen for mAb 545 was obtained from the reduced product of the PF3 fraction of human amniotic membrane prepared as previously described (Maddox et al., *J. Biol. Chem.* 261:21381–21385 (1989)). Briefly, disulfide bonds of the PF3 fraction were reduced and alkylated with vinyl pyridine. Peptides containing cysteine residues were reduced in 100 fold molar excess of 2-mercaptoethanol overnight at room temperature in 0.5M TrisHCl buffer, pH 7.5, containing 0.2M NaCl and 5 mM EDTA. Equimolar amounts of vinyl pyridine to mercaptoethanol were added and after a further 90 minute incubation at room temperature, the peptides were separated from excess reagent by gel filtration, and utilized for immunization of BALB/c mouse as previously described (Sakai et al., J. Cell Biol. 103:1577–1586 (1986)). Mab 545 has been shown to specifically immunoprecipitate laminin from a complex mixture of proteins in radiolabeled keratinocyte conditioned medium. Additionally, this antibody has been shown to have a staining pattern identical to polyclonal anti-laminin antibody on human skin sections by indirect immunofluorescent microscopy.

The 4E10 mAb, specific for the laminin B1 chain, is described in (Weaver et al., *J. Biol. Chem.* 258:12654–12660 (1983)).

mABs C1 which reacts with B1s and C4 which reacts with the B1s chain were from Dr. J. Sanes of the Washington School of Medicine, St. Louis.

Laminin B2 Abs

Laminin B2 chain specific mAb 2E8, Engvall et al., *J. Cell Biol.* 103:2457–2465 (1986) were provided by Dr. Eva Engvall of the La Jolla Cancer Research Foundation and have been described.

Laminin A Abs

Anti merosin mAb 5H2 is described in Leivo et al., *Lab Invest.* 60:783–790 (1989).

The lamin A chain specific mAbs 1F5, 11D5 (Engvall, et al., *Cell Regul* 1:731–740 (1990); and 4C7, Engvall et al., *J. Cell Biol.* 103:2457–2465 (1986) were provided by Dr. Eva Engvall of the La Jolla Cancer Research Foundation and have been described.

mAb 1924 specific for the Ae-chain of laminin was purchased from Chemicon.

Other

Affinity purified polyclonal antibody against mouse laminin was obtained from Sigma Chemical Company, St. Louis, Mo. Monoclonal antibodies were purified from hybridoma medium as previously described (Keene et al., 1991).

KS-laminin and KS-laminin-Kalinin Adduct

The materials contained in MONO-Q™ peak 1 were evaluated by SDS-PAGE prior to disulfide bond reduction. Three major bands were observed. The slowest migrating band (referred to as band A) migrated only a short distance into the running gel, and while its mass could not be accurately estimated, it is greater than observed for monomeric laminin. The second band (referred to as band B) migrated to a position expected for a K-laminin monomer (about 600–700kDa). The third band was very near the dye front, and was not further characterized.

The chain compositions of the bands A and B were determined following electrophoretic resolution of the reduction product of the excised gel band, followed by immunoblotting. Bands A and B, were both immunoreactive before and after reduction with mAb C4 (demonstrating the presence of B1s) and polyclonal anti-laminin. After reduction, both A and B could be resolved into bands of 220, 190, 165, and 145 kDa. B included additional bands at 105 and 140 kDa. Following reduction, the 220 kDa band of A and B was reactive with anti-laminin, and the 190kDa band of A and B was recognized by anti-B1s. In no case was a band in the position of Ae or B1e recognized by anti-laminin antibodies in either peak. The remaining unidentified bands at 165 and 145kDa in band A were identified as the kalinin A chain by immunoblotting with antibody BM-165, but the kalinin B1 chain was not present by immunoblot analysis nor was the kalinin B2 chain present by Coomassie blue staining or by immunoblot with polyclonal anti-kalinin. Therefore, band B contains a disulfide bonded aggregate of Ak, B1s, B2e chains. The amounts of 165 plus 145 are approximately equal to that of 220 or 190kDa, suggesting that each chain is present in equimolar amounts, consistent with their assembly into a cruciform laminin molecule. Rotary shadowed images of the materials in MONO-Q™ peak 1 showed Y-shaped molecules consistent with the molecular shape expected for a molecule containing these chains. This molecule was named KS-laminin.

Following disulfide bond reduction, electrophoretic band A contained bands in the position of B2e, B1s, the kalinin A chain (165/145kDa), the kalinin B1 chain (140kDa) and the kalinin B2 chain (105kDa). The identification of these chains was confirmed by Western blotting. The 220kDa band was recognized by polyclonal anti-laminin and is in the position of the B2e chain. The 190kDa chain was recognized by mAb C4 as B1s. The 165 and 145kDa bands are recognized by mAb BM-165 as the kalinin A chain. The 140 kDa band blotted by mAb BM-140 specific for the kalinin B1 chain, and the 105kDa chain is recognized by polyclonal anti-kalinin and is in the position expected for the kalinin B2 chain. These data indicate that band A represents a disulfide-bonded-dimer of one molecule of kalinin with one molecule of KS-laminin. Rotary shadow image analysis of MONO-Q™ peak 1 is consistent with this interpretation. In addition to Y-shaped molecules, prominent image of an aggregate with two long arms and two short arms is present. Globular domains consistent in size with laminin A chain G domains are present at the ends of the long arms. The images suggest that kalinin associates with the Ak, B1s, B2e molecule through the truncated short arms at the intersection of the long and short arms of KS-laminin.

No monomeric kalinin molecules were seen in the rotary shadowed images of MONO-Q™ peak 1, nor were kalinin B1 or B2 chains detected in the monomeric gel band, or in the monomeric band obtained from peak 2 suggesting that kalinin in the tissue is all present in a complex with either K-laminin or KS-laminin.

The complex of KS-laminin with kalinin is most likely to derive from an interaction of the kalinin B1 chain VI domain with the kalinin A chain short arm domain in KS-laminin. This prediction reflects the interpretation of the rotary shadowed image of the complex as the short arm of kalinin interacting with a KS-laminin domain near the intersection of the KS-laminin short arms. Support for a role of the kalinin B1 chain VI domain comes from the presence of an unpaired cysteinyl residue in that domain (Gerecke et al, 1994), and the absence of any other globular domain at the N-terminus of the fully processed kalinin molecule. The contributor of the other unpaired cysteine from KS-laminin is not known, but since complex formation between kalinin and other laminins has only been seen between kalinin A chain containing laminins (i.e. K-laminin and KS-laminin) despite the fact that other laminin are present within the basement membranes of skin and amnion, the most likely bonding partner for the B1k VI domain is the kalinin A chain.

The following procedures were performed as previously described: SDS-PAGE (Laemmli, 1970), electrophoretic transfer of proteins to nitrocellulose with immunoblot analysis (Lunstrum et al., 1986), indirect immunofluorescent microscopy of frozen sections of human tissue (Sakai et al., 1986).

Rotary-shadow analysis and length measurements have been detailed elsewhere (Morris et al., *J. Biol. Chem.* 261:5638–5644 (1986); Lunstrum et al., *J. Biol. Chem.* 261:9042–9048 (1986); and Bachinger et al., *J. Biol. Chem.* 265:10095–10101 (1990)). Briefly, rotary shadowing of molecules was accomplished using a modification of standard techniques described by Shotton et al., *J. Mol. Biol.* 131:303–329 (1979) and Tyler et al., *J. Ultrastruct. Res.* 71:95–102 (1980). Samples in 0.15-M carbonate buffer, pH 7.4, were diluted with glycerol to a final concentration of 70%. Then, 1200 µL of solution was sprayed through an airbrush at an acute angle onto freshly cleaved 6-mm diameter mica discs. Droplet diameters were 50–200 µm. Samples were dried in an evaporator at $10^{-6}$ Torr. Platinum wire was wrapped around the carbon electrodes and the sample was placed on the stage and rotated at 100 rpm. At high voltage, the platinum was evaporated to completion at a 6-degree angle from the mica surface. The stage was then tilted 90 degrees relative to a carbon source and the chamber was evacuated. A 50-Å layer of carbon was evaporatively deposited onto the surface of the mica to from a "carbon replica." The carbon replica was immediately floated off the mica by carefully immersing the carbon-coated mica in double-distilled water. The carbon replicas were mounted onto 400-mesh grids. The replicas were examined using a transmission electron microscope at 80 KV with a 30 µm objective aperture.

Tissue Distribution of KS-laminin

The observation of B1s in the amniotic extracts was unexpected, since no B1s was seen in similar preparations from human skin, or in the culture medium of human keratinocytes. The distribution of B1s was therefore examined in skin and in amnion.

Full term human amnion was immunostained using antibodies specific for kalinin (BM-165), B1s (C1 , C4), type VII collagen (NP-185), laminin Ae chain (mAb 1924), and laminin B1e chain (mAb 545). The B1s chain is visualized only at the epithelial-stromal interface, equivalent to the distribution of type VII collagen and kalinin, and is not present in the capillary beds stained by type IV collagen and laminin.

Similar staining of human foreskin with the same antibodies showed the expected distributions for kalinin, type VII collagen, and laminin (Ac chain and B1e chain). B1s staining was observed around nerves, but was absent or only weakly present at the dermal-epidermal junction. This is in contrast to what is seen in fetal bovine skin. In this case, B1e is distributed around nerves and at the dermal-epidermal junction.

Enbloc immunolocalization of antigens was performed as previously described by Keene et al., *J. Cell Biol.* 104:611–621 (1987), with some modifications as follows:

Human neonate foreskins collected shortly after circumcision were cut into 0.5 mm×1 mm blocks, all including epithelium, and washed for two hours in phosphate buffered saline (PBS), pH 7.4 at 4° C., rinsed in several changes of PBS over 6 hours, then incubated overnight at 4° C. in 1-nm gold-conjugated secondary antibody (Janssen Life Sciences Products, Piscataway, N.J.) diluted 1:3 in PBS containing 1.0% BSA (bovine serum albumin). Following washing, the foreskin tissues were submersed in ice-cold silver intensification solution (Janssen Life Sciences Products, Piscataway, N.J.) for 15 minutes, then rapidly warmed to room temperature. After allowing silver to precipitate upon the 1-nm gold particles for seven minutes at room temperature, the tissues were rinsed several times over a 15-minute period with water, then rinsed with 0.1M cacodylate buffer at pH 7.4. The tissues were finally fixed in 0.1-M cacodylate-buffered 1.5%/1.5% glutaraldehyde/paraformaldehyde, pH 7.4, dehydrated in a graded series of ethanol dilutions, exposed to propylene oxide, and embedded in Spurrs epoxy.

Control antibodies used included those recognizing elastin (produced and provided by Dr. Lynn Sakai), collagen type IV (Sakai et al, *Am. J. Pathology* 108:310–318 (1982)), and collagen type VI (Keene et al., *J. Cell. Biol.* 107:1995–2006 (1988)).

Function

The B1e chain has been shown to mediate laminin polymerization in vitro through interactions of the VI domain. The rat B1s chain VI domain shares 70% sequence identity with the human B1e VI domain, strongly suggesting that B1s participates in S-laminin polymerization. B1e has also been implicated in cell binding through the amino acid sequences at positions 902–906 and 929–933 of B1e in the 9th EGF repeat of domain III. These sequences are not found in B1s, yet the cell attachment activity of B1e and B1s laminins are indistinguishable. Two activities have been reported to be specific to the B1s chain: adhesion of ciliary ganglion neurons to the sequence LRE in B1s, and the in vitro binding of B1s containing placental laminin to BM-90. The physiological significance of these observations is not known.

No monomeric kalinin was detected in the solubilized amnion. While considerable amounts of monomeric K-laminin and KS-laminin were observed, all of the kalinin was seen complexed to either K-laminin or to KS-laminin. This is consistent the model that kalinin alone cannot generate dermal-epidermal stability. The severe truncation of the kalinin short arms, especially following processing, deprives the molecule of the domains believed to be necessary for nidogen binding and self-polymerization. Assuming the G domain of the kalinin A chain is the primary site of cell binding, then the kalinin molecule must strongly interact with another species to bind components of the basement membrane. The observed covalent association with K-laminin and KS-laminin fill this requirement. The B2e chain of K- and KS-laminin provides the binding site for nidogen, which binds type IV collagen and perlecan. The VI domains of B2e, B1e, and B1s provide sites for polymerization. Thus, in combination with K- and KS-laminin, kalinin is able to mediate binding of the epithelial cell to the basement membrane. The anchoring fibrils secure the basement membrane to the dermis through interactions of the NC-1 domain of type VII collagen with laminin and type IV collagen. It is likely that type VII collagen interacts directly with KS-laminin complex.

Protein Sequence

The protein sequencing was done according to Aebersold et al (1987). The complex KS laminin-Kalinin was run on a polyacrylamide gel in presence of 2-mercaptoethanol and transblotted to a nitrocellulose membrane (Biorad). The 190 kDa band was excised and digested by the protease Lys-C. The digest product was separated by HPLC and one fragment was sequenced on an Applied Biosystem gas phase sequencer. The sequence corresponded to the B1s sequence published by Hunter et al. (1989).

EXAMPLE 1

One method of keratinocyte transplantation was disclosed by O'Connor et al., *The Lancet* 1:75–78 (1981). According to this method, a patient has two 2 cm$^2$ skin samples removed under local anesthesia. The tissue is then placed in culture medium and transferred to a laboratory for cultivation and graft preparation. As much subcutaneous tissue and dermis as possible is removed from the tissue, and the tissue is then minced and trypsinized. The cells are inoculated at different densities (from $10^4$ to $10^6$ per 50-mm diameter dish containing $4 \times 10^5$ lethally irradiated 3T3 cells). The cultures are supplied with fortified Eagle's medium supplemented with 20% fetal calf serum, 0.4 µg/mL hydrocortisone, and 0.1 nmol/L choleragen. The cultures are incubated at 30° C. in a 10% $Co_2$ atmosphere. After three days, epidermal growth factor (EFG 10 ng/mL) is added to the culture medium. The medium is changed twice weekly until the cultures either become confluent (between 14 and 21 days) or are subcultured. Some subconfluent cultures are viably frozen and later subcultured so that secondary and tertiary subcultures can be prepared for later use as grafts.

The confluent epithelial cells are detached in their confluent state from the surface of the culture dishes using the enzyme dispase. After detachment, each elastic epithelium shrinks to a diameter of 2 to 2.5 cm. Each epithelium is then washed with serum-free medium and placed basal-side up on two layers of sterile vaseline gauze cut into 2-cm diameter circles. Sufficient serum-free medium is added to cover the exposed basal surface. Several dishes containing grafts are then placed in a glass jar; the atmosphere in the jar is flushed with 10% $CO_2$ and the sealed jar is transported to the bedside.

Epithelial grafts including the vaseline gauze covering are placed on prepared wound sites with the basal cell layer directed against the wound surface. No suturing is necessary if the grafts are held in place by a single layer of non-impregnated fine mesh gauze, which is overlayed with a loose layer of coarse mash gauze that is changed daily. The fine mesh gauze and the vaseline gauze are removed between the sixth and tenth days and the area is redressed with a single layer of vaseline gauze and a loose layer of coarse gauze. Three dressings are changed daily for three to four weeks from the time of grafting. Thereafter, the grafts are left exposed to the atmosphere, but treated with a thin layer of lanolin ointment once daily.

The epithelial grafts described above can be placed on three different types of "recipient beds" (wound surfaces): early granulation tissue (less than 7 days old), chronic granulation tissue, and areas recently excised down to the facia.

In accordance with the present invention, adhesion of the confluent epithelium to the underlying tissue can be improved by applying molecules of the invention either on the basal face of the keratinocyte culture or on the epithelium of the exposed surface of the tissue on which the graft is being placed. Such exogenous KS-laminin will provide superior adhesion.

Alternatively, a molecule of the invention is applied between the cultured keratinocytes and the epithelium, preferably in a such as PBS containing physiological amounts of $Ca^{++}$ and $Mg^{++}$ (e.g., 0.7–1.1 mmol/L $Mg^{++}$ and 1–3 mmol/L $Ca^{++}$). The adhesion proteins can be suspended in PBS with Ca++ and Mg+++, then introduced into a gelatin or propylene glycol base for topical application.

EXAMPLE 2

Methods of grafting autologous cultured human epithelium according to the present invention can be performed as follows: First, a 2 cm$^2$ full-thickness biopsy specimen of skin is removed from the axilla of each patient. The skin is minced and trypsinized to produce a single cell suspension. Aliquots of $2 \times 10^6$ cells are frozen and stored or cultured in flasks with a surface area of 75 cm$^2$. When the colonies become confluent (approximately 10 days), the cultures are trypsinized, and $3 \times 10^5$ cells are inoculated to make secondary and tertiary cultures for grafting. To prepare grafts, the cultured sheets of cells are released from the flasks with dispase, washed with medium, and applied to petrolatum gauze cut to 4.5×6 cm. Burn wounds are excised to muscle fascia or, in the case of third-degree burns, are excised tangentially to a depth sufficient to remove dead tissue. The cultured grafts with their gauze backing are placed on prepared wound surfaces, sutured in place, and dressed with dry gauze. The petrolatum gauze is removed seven to ten days later.

According to the present invention, the foregoing procedure would be modified by administering molecules of the invention at the interface of the cultured graft and the wound surface.

EXAMPLE 3

Kalinin or Kalinin-containing molecules may be deficient or altered in individuals with certain blistering conditions such as junctional epidermolysis bullosa (Eady, *Clin. Exp. Dermatol.* 12:161–170 (1987)) or herpes gestationis (Katz et al. (eds.), *Dermatology in General Medicine,* McGraw-Hill, New York, 586–588 (1987)). Hence, topical application of molecules of the invention may also be useful in treating these conditions to improve adherence between the dermis and epidermis.

EXAMPLE 4

Standard in vitro attachment assays can be performed to determine that purified KS laminin facilitates keratinocyte attachment to plastic substrates. In these assays, exogenous purified KS-laminin or control proteins are incubated overnight with the substrate, and the plates are then washed. Unattached cells are washed away, and the remaining attached cells are quantified, as described in Aumailley et al., *Exp. Cell, Res.* 181:463–474 (1989).

EXAMPLE 5

The role of a molecule of the invention in enhancing keratinocyte attachment to a substrate can be assessed by treating cell sheets with dispase to release them from a plastic or glass substrate, as would be done in preparing transfer sheets to a wound bed. The substrates are coated either with a molecule of the invention or control proteins. The adherence of the cell sheet is evaluated morphologically to demonstrate that the sheet has superior adherence to the KS-laminin or KS-laminin kalinin adduct coated substrate. The adherence of the sheet is also evaluated by indirect immunofluorescence using the BM165 mAb. Firmly attached cell sheets will not allow antibody penetration to the substrate surface as demonstrated by the studies of confluent keratinocyte cultures. Fluorescence beneath the cells will be observed for less firmly attached sheets.

EXAMPLE 6

Animal studies can be performed to show the effectiveness of molecules of the invention to promote the adhesion of human keratinocytes to a wound bed. Suitable wound beds include areas of excised epidermis, or burns that have left an underlying dermal area exposed.

KS-laminin and/or KS-laminin-kalinin adduct can be purified from amnion, using immuno-affinity columns bearing the BM-165 monoclonal antibody that recognizes the "A"-like chain of kalinin, K-laminin and KS-laminin. These molecules will be retained by the matrix and eluted with 0.1M acetic acid and immediately neutralized. The resulting mixture of KS-laminin, K-laminin and kalinin will be further fractioned by immuno-affinity with a column bearing a monoclonal antibody that recognizes only the BIS chain of KS-laminin. Pure KS-laminin will be eluted from the column. The procedure will be repeated until pure KS-laminin is obtained as judged by western analysis. The adduct will be solubilized from human amnion following extensive collagenase digestion as described by Bächinger (1990) *J. Biol. Chem.* 265:10095–10101, which is incorporated by reference. If insufficient amount of kalinin and KS-laminin is obtained, then the disulfide bond joining the two molecules in the purified adduct can be selectively reduced by incubation with 1–10 mM cysteine, while retaining the native conformation. The reduction products will be fractionated as described above.

Nude mice each receive 4 full thickness skin wound 1 cm$^2$ each. The wounds are administered on the back, two on each side of the spinal midline under anesthesia. The wounds are immediately treated as described below, and the mice are allowed to recover for 1–5 days under mild anesthesia to prevent trauma to the wound surface.

The gel-suspensions will be applied to the fresh wounds. The 0 mg/ml molecular suspension will always be applied to wounds on the left side of the mouse. One mouse per molecular concentration will be used.

OTHER EMBODIMENTS

The invention includes: allelic variations; natural mutants; induced mutants, and polypeptides or proteins specifically bound by antisera specific for KS-kalinin.

Other embodiments are within the following claims:

What is claimed is:

1. Isolated and purified KS-laminin consisting of:

a B1s chain which reacts with an antibody to the B1s chain of S-laminin, a B2e chain which reacts with an antibody to the B2e chain of EHS-laminin, an A chain which reacts with an antibody to the kalinin A chain;

wherein the B1s, B2e and kalinin A chains have molecular weights of about 190, 220 and 165 as determined by SDS-PAGE under denaturing conditions and wherein the B1s, B2e and kalinin A chains are present in a ratio of about 1 B1s to 1 B1e to 1 kalinin A.

* * * * *